United States Patent
Patil et al.

(10) Patent No.: US 11,193,079 B2
(45) Date of Patent: Dec. 7, 2021

(54) GLYCOL ETHER NEO-ESTERS, LUBRICATING OIL COMPOSITIONS CONTAINING SAME AND PROCESSES FOR MAKING SAME

(71) Applicant: ExxonMobil Research and Engineering Company, Annandale, NJ (US)

(72) Inventors: Abhimanyu O. Patil, Westfield, NJ (US); Satish Bodige, Wayne, NJ (US); Kyle G. Lewis, Houston, TX (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 0 days.

(21) Appl. No.: 15/930,012

(22) Filed: May 12, 2020

(65) Prior Publication Data

US 2020/0399552 A1 Dec. 24, 2020

Related U.S. Application Data

(60) Provisional application No. 62/864,680, filed on Jun. 21, 2019.

(51) Int. Cl.
| | |
|---|---|
| *C10M 129/76* | (2006.01) |
| *C10M 105/34* | (2006.01) |
| *C07C 69/708* | (2006.01) |
| *C07C 67/48* | (2006.01) |
| *C10N 30/00* | (2006.01) |
| *C10N 20/00* | (2006.01) |
| *C10N 20/02* | (2006.01) |
| *C10N 40/25* | (2006.01) |

(52) U.S. Cl.
CPC ............ *C10M 105/34* (2013.01); *C07C 67/48* (2013.01); *C07C 69/708* (2013.01); *C10M 2207/2815* (2013.01); *C10N 2020/02* (2013.01); *C10N 2020/065* (2020.05); *C10N 2030/74* (2020.05); *C10N 2040/25* (2013.01)

(58) Field of Classification Search
CPC ......... C10M 105/34; C10M 2207/2815; C07C 67/48; C07C 69/708; C10N 2040/25; C10N 2030/74; C10N 2020/02; C10N 2020/065
USPC .......................................................... 508/501
See application file for complete search history.

(56) References Cited

U.S. PATENT DOCUMENTS

2017/0183595 A1* 6/2017 Ng ....................... C10M 105/34

OTHER PUBLICATIONS

A. O. Patil et al., "Ester Compounds, Lubricating Oil Compositions Containing Same and Process for Making Same", U.S. Appl. No. 62/551,068, filed Aug. 28, 2017.
A. O. Patil et al., "Ester Compounds, Lubricating Oil Compositions Containing Same and Process for Making Same", U.S. Appl. No. 62/565,536, filed Sep. 29, 2017.
A. O. Patil et al., "Ester Compounds, Lubricating Oil Compositions Containing Same and Process for Making Same", U.S. Appl. No. 62/565,548, filed Sep. 29, 2017.
A. O. Patil et al.,"Neo-Alcohol Compounds, Processes for Making Same and Use Thereof", U.S. Appl. No. 62/565,501, filed Sep. 29, 2017.

* cited by examiner

*Primary Examiner* — James C Goloboy
*Assistant Examiner* — Francis C Campanell
(74) *Attorney, Agent, or Firm* — Robert A. Migliorini

(57) ABSTRACT

Compositions include ether ester compounds derived from neo-acids, lubricating oil base stocks containing such ester compounds, and lubricating oil compositions containing such ester compounds. Methods can include making and formulating compositions containing ether ester compounds derived from neo-acids.

24 Claims, No Drawings

GLYCOL ETHER NEO-ESTERS, LUBRICATING OIL COMPOSITIONS CONTAINING SAME AND PROCESSES FOR MAKING SAME

FIELD

The present disclosure relates to ester compounds of neo-acids, lubricating oil base stocks and lubricating oil compositions containing such ester compounds, and processes for making them.

BACKGROUND

Polyalpha-olefins ("PAOs") are important lubricant base stocks with excellent lubricant properties, including high viscosity index ("VI"), low volatility and are available in various viscosity ranges (e.g., kinematic viscosity at 100° C. in the range of 2 to 300 cSt). However, PAOs are paraffinic hydrocarbons with low polarity. This low polarity leads to low solubility and dispersancy for polar additives or sludge generated during service. To compensate for this low polarity, lube formulators add one or multiple polar co-base stocks. For example, ester or alkylated naphthalene is often present at 1 to 50 wt % levels in many finished lubricant formulations to increase the fluid polarity which improves the solubility of polar additives and sludge.

Lubricants in commercial use today are often prepared from a variety of natural and synthetic base stocks admixed with various additive packages and solvents depending upon their intended application. The base stocks typically include mineral oils, polyalpha-olefins (PAO), gas-to-liquid (GTL) base oils, silicone oils, phosphate esters, diesters, polyol esters, and the like. In addition, high oxidation stability is generally desirable for a base stock in order to impart a long service life to engine oils.

A trend for passenger car engine oils (PCEOs) is an overall improvement in quality as higher quality base stocks become more readily available. Typically the highest quality PCEO products are formulated with base stocks such as PAOs or GTL stocks admixed with various additive packages.

Furthermore, fuel/energy efficiency has been identified as an important feature for lubricants. However, in order to provide step-out fuel economy while maintaining or improving other lubricant performance features, base stocks with lower friction coefficients are needed. Low friction coefficients and low viscosity at all temperature ranges are important properties which contribute to lubricant fuel economy.

Improving heat transfer is also an emerging need as the energy density of systems and equipment increases, where improving thermodynamic efficiency is often coupled with higher operating temperatures. There are also developing requirements to provide cooling fluids for hybrid and electric vehicles. Currently traditional cooling fluids, including formulated lubricants, can be used but have limited properties.

Therefore, there is a need for cost compatible, polar co-base stocks to improve solvency of these fluids and that also exhibit suitable heat transfer fluid properties that meet industrial requirements for energy density, specific heat capacity, and thermal conductivity. Moreover, in order to formulate ultra-low viscosity engine oil lubricant for step-out fuel economy benefit, it is desirable to have low viscosity base stocks.

SUMMARY

It has been found that esters of neo-acids can be advantageously used as lubricating oil base stocks with desirable lubricating oil properties such as polarity and oxidation stability.

Provided herein are compounds of structural Formula F-I:

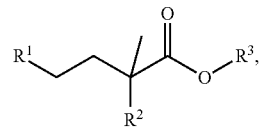

wherein $R^1$ and $R^2$ are independently each a hydrocarbyl group comprising at least two carbon atoms; and $R^3$ is a glycol ether or a polyglycol ether. In an aspect, $R^1$ and $R^2$ are each independently a C2 to C30 linear or branched alkyl group. In an aspect, at least one of $R^1$ and $R^2$ is a linear alkyl group. In an aspect, at least one of $R^1$ and $R^2$ is selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl. In an aspect, at least one of $R^1$ and $R^2$ is selected from n-butyl, n-hexyl, n-octyl, n-decyl, and n-dodecyl. In an aspect, $R^1$ and $R^2$ are each independently a branched alkyl group selected from 2-ethylhexyl, 2-propylheptanyl, 2-butyloctyl and 3,5-dimethyloctyl. In an aspect, $R^1$ and $R^2$ are identical. In an aspect, $R^3$ is a glycol ether of the structural formula:

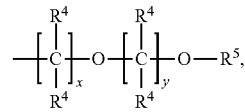

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, and y is a value from about 1 to about 10. In an aspect, $R^3$ comprises 2 to 24 carbon atoms. In an aspect, $R^3$ is a polyglycol ether of the structural formula:

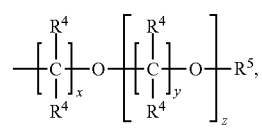

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, y is a value from about 1 to about 10, and z is a value from about 0 to about 100. In an aspect, $R^3$ is one or more selected from a group of methoxyethanol, ethoxyethanol, propoxyethanol, butoxyethanol, pentoxyethanol, hexyloxyethanol, phenoxyethanol, diethylene glycol methyl ether, diethylene glycol ethyl ether, diethylene glycol propyl ether, diethylene glycol butyl ether, diethylene glycol pentyl ether, diethylene glycol hexyl ether, diethylene glycol benzyl ether, triethylene glycol methyl ether, triethylene glycol ethyl ether, triethylene glycol propyl ether, triethylene glycol butyl ether, triethylene glycol pentyl ether, triethylene glycol hexyl ether, triethylene glycol benzyl ether, tetraethylene glycol methyl ether, tetraethylene glycol ethyl ether, tetraethylene glycol propyl ether, tetraethylene glycol butyl ether, tetraethylene glycol pentyl ether, tetraethylene glycol hexyl ether, tetraethylene glycol benzyl ether, propylene glycol methyl ether, propylene glycol ethyl ether, propylene glycol propyl ether, propylene glycol butyl ether, propylene glycol hexyl ether, propylene glycol benzyl ether, dipropylene glycol methyl ether, dipropylene glycol propyl ether, dipropylene glycol butyl ether, dipropylene glycol pentyl ether, dipropylene glycol hexyl ether, and dipropylene glycol benzyl ether.

In an aspect, the compound of Formula F-I is 2-(2-(2-hexyloxyethoxy)ethoxy)ethyl 2-methyl-2-octyldecanoate, 2-(2-(2-hexyloxyethoxy)ethoxy)ethyl 2-methyl-2-hexyloctanoate, 2-(2-(3-hexyloxypropoxy)ethoxy)ethyl 2-ethyl-2-octyldecanoate, 2-(3-(2-hexyloxyethoxy)propoxy)ethyl 2-ethyl-2-octyldecanoate, 2-(3-(3-hexyloxypropoxy)propoxy)ethyl 2-ethyl-2-octyldecanoate, 2-(2-(2-butyloxyethoxy)ethoxy)ethyl 2-methyl-2-octyldecanoate, 2-(2-(2-butyloxyethoxy)ethoxy)ethyl 2-methyl-2-hexyloctanoate, 2-(2-(3-butyloxypropoxy)ethoxy)ethyl 2-ethyl-2-octyldecanoate, 2-(3-(2-butyloxyethoxy)propoxy)ethyl 2-ethyl-2-octyldecanoate, 2-(3-(3-butyloxypropoxy)propoxy)ethyl 2-ethyl-2-octyldecanoate, 2-(2-(2-ethoxyethoxy)ethoxy)ethyl 2-methyl-2-octyldecanoate, 2-(2-(2-ethoxyethoxy)ethoxy)ethyl 2-methyl-2-hexyloctanoate, 2-(2-(3-ethoxypropoxy)ethoxy)ethyl 2-ethyl-2-octyldecanoate, 2-(3-(2-ethoxyethoxy)propoxy)ethyl 2-ethyl-2-octyldecanoate, and 2-(3-(3-ethoxypropoxy)propoxy)ethyl 2-ethyl-2-octyldecanoate. Also provided herein are lubricating oil composition comprising one or more compounds of Formula I. In an aspect, the lubricating composition is a lubricating oil base stock. In an aspect, the lubricating oil composition has a kinematic viscosity at 100° C. as determined pursuant to ASTM D445 in the range from 1 to 40 cSt. In an aspect, the concentration of the first base stock, based on the total weight of the lubricating oil formulation, is in the range from 5 to 95 wt %.

Also provided herein are methods of making compounds of Formula F-I as well as the lubricating compositions comprising the same.

Further features and advantages of this disclosure will be understood by reference to the following drawings and detailed description.

DETAILED DESCRIPTION

Definitions

In this disclosure, the indefinite article "a" or "an" means at least one, unless it is clearly specified or indicated by the context to mean one.

"Alkyl group" refers to a saturated hydrocarbyl group of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms.

"Cycloalkyl group" refers to an alkyl group in which all carbon atoms form a ring structure. Non-limiting examples of cycloalkyl groups include cyclopentyl, cyclohexyl, decahydronaphthalen-1-yl, spiro[5.5]undecan-3-yl, and the like.

"Aryl group" refers to an unsaturated, cyclic hydrocarbyl group of carbon and hydrogen atoms in which the carbon atoms join to form a conjugated π system. Non-limiting examples of aryl groups include phenyl, 1-naphthyl, 2-naphthyl, 3-naphthyl, and the like.

"Arylalkyl group" refers to an alkyl group substituted by an aryl group or alkylaryl group. Non-limiting examples of arylalkyl group include benzyl, 2-phenylethyl, 4-phenylbutyl, and the like.

"Alkylaryl group" refers to an aryl group substituted by an alkyl group. Non-limiting examples of alkylaryl group include 2-methylphenyl, 3-methylphenyl, 4-methylphenyl, 2-methyl-1-naphtyl, 6-phenylhexyl, 5-pentylphenyl, 4-butylphenyl, 4-terterybutylphenyl, and the like.

"Cycloalkylalkyl group" refers to an alkyl group substituted by a cycloalkyl group or an alkylcycloalkyl group. An example of cycloalkylalkyl group is cyclohexylmethyl, and the like.

"Alkylcycloalkyl group" refers to a cycloalkyl group substituted by an alkyl group. Non-limiting examples of alkylcycloalkyl group include 2-methylcyclohexyl, 3-methylcyclohexyl, 4-methylcyclohexyl, 4-tertiary butyl cyclohexyl, and the like.

"Glycol ether" refers to an ether group having a structure corresponding to the following formula:

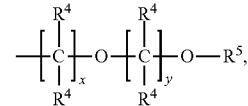

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted ear unsubstituted alkyl group (C1-C30), alkenyl group (C1-C30), alkoxy group (C1-C30), aryl group (C4-C30), or arylalkyl group (C5-C30), x is a value from about 0 to about 10, and y is a value from about 1 to about 10.

"Polyglycol ether" refers to an ether group having a structure corresponding to the following formula:

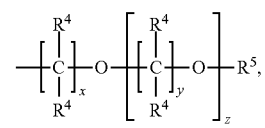

where each R4 is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, y is a value from about 1 to about 10, and z is a value from about 0 to about 100.

"Hydrocarbyl group" refers to a group of hydrogen and carbon atoms only. A hydrocarbyl group can be saturated or unsaturated, linear or branched, cyclic or acyclic, containing a cyclic structure or free of cyclic structure, and aromatic or non-aromatic. A "substituted" hydrocarbyl group is a hydrocarbyl group in which a hydrogen atom is substituted by any another group. An "unsubstituted" hydrocarbyl group is a hydrocarbyl group.

"Cn" group or compound refers to a group or a compound containing carbon atoms at total number thereof of n. Thus, "Cm-Cn" or "Cm to Cn" group or compound refers to a group or compound containing carbon atoms at a total number thereof in the range from m to n. Thus, a C1-C50 alkyl group refers to an alkyl group containing carbon atoms at a total number thereof in the range from 1 to 50.

"Mono-ester" refers to a compound having one ester (—C(O)—O—) functional group therein.

"Gamma-branched alcohol" refers to an alcohol having a structure corresponding to the following formula:

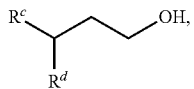

where $R^c$ and $R^d$ are independently linear, branched, cyclic, substituted or unsubstituted hydrocarbyl groups containing from d1 to d2 carbon atoms, where d1 and d2 can be, independently, 1, 2, 3, 4, 5, 6, 7, 8, 9, 10, 15, 20, 25, 30, 35, 40, 45, 50, 55, 60, 65, 70, 75, 80, 85, 90, 95, 100, as long as d1<d2. In an aspect, d1=2 and d2=50. In an aspect, $R^c$ and $R^d$ are alkyl groups. In an aspect, $R^c$ and $R^d$ are linear or branched alkyl groups. In an aspect, $R^c$ and $R^d$ differ in terms of total number of carbon atoms contained therein by two (2).

"Neo-acid" refers to a carboxylic acid having the following general structure:

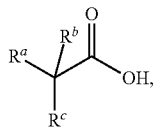

where $R^a$, $R^b$, and $R^c$, the same or different, are independently hydrocarbyl groups.

"SAE" refers to SAE International, formerly known as Society of Automotive Engineers, which is a professional organization that sets standards for internal combustion engine lubricating oils.

"SAE J300" refers to the viscosity grade classification system of engine lubricating oils established by SAE, which defines the limits of the classifications in rheological terms only.

"Lubricating oil" refers to a substance that can be introduced between two or more surfaces and lowers the level of friction between two adjacent surfaces moving relative to each other. Non-limiting examples of lubricating oils include those in liquid form during normal use thereof such as engine oils and gear box oils and those in viscous liquid form during normal use such as grease. A lubricating oil "base stock" is a material, typically a fluid at various levels of viscosity at the operating temperature of the lubricating oil, used to formulate a lubricating oil by admixing with other components. Non-limiting examples of base stocks suitable in lubricating oils include API Group I, Group II, Group III, Group IV, and Group V base stocks. If one base stock is designated as a primary base stock in the lubricating oil, any additional base stock may be called a co-base stock.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

All Noack volatility ("NV") values in this disclosure are as determined pursuant to ASTM D5800 unless specified otherwise. Unit of all NV values is wt %, unless otherwise specified.

All percentages in describing chemical compositions herein are by weight unless specified otherwise. "Wt %" means percent by weight.

"Consisting essentially of" means containing at a concentration by weight of at least 90 wt %, based on the total weight of the mixture in question. Thus, a lubricating oil base stock consisting essentially of a given ester compound comprises that ester compound at a concentration by weight of at least 90 wt %, based on the total weight of the lubricating oil base stock.

All numerical values within the detailed description and the claims herein are modified by "about" or "approximately" the indicated value, taking into account experimental error and variations that would be expected by a person having ordinary skill in the art.

The Neo-Acid Ester Compounds

Compounds in accordance with the present disclosure can be used to prepare polar base stock fluids that provide appropriate solubility and dispersancy for polar additives or sludge generated during service of lubricating oils as well as a high oxidation stability.

Provided herein are a class of compounds defined by structural Formula F-I as follows:

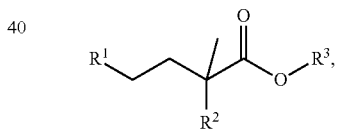

wherein $R^1$ and $R^2$ are each independently a hydrocarbyl group containing at least 2 carbon atoms therein, which can include a C2 to C60 hydrocarbyl group such as a C2 to C60 alkyl group, a C2 to C60 linear or branched alkyl group, and a C2 to C30 linear or branched alkyl group); and $R^3$ is a glycol ether or a polyglycol ether. To the extent this compound can be considered as an ester derived from a neo-acid, it will be referred to as such in this disclosure, and also as "ester of this disclosure" herein.

In an aspect, $R^1$ and $R^2$ each independently include c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, or 60, as long as c1<c2. In an aspect, c1=2 and c2=30. In another aspect, c1=2 and c2=24. In another aspect, c1=4, and c2=16. In yet another aspect, c1=4, and c2=12. In an aspect, $R^1$ and $R^2$ each independently comprise even number of carbon atoms.

At least one of $R^1$ and $R^2$ (or both $R^1$ and $R^2$ independently each) can be a branched alkyl group, such as a branched alkyl group of the structural Formula F-IV as follows:

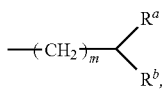

where $R^a$ and $R^b$ are independently hydrocarbyl groups, including alkyl groups, such as linear or branched alkyl groups. In an aspect, $R^a$ and $R^b$ are linear alkyl groups, m is a non-negative integer, including a non-negative integer satisfying an inequality selected from any one of m≥2, m≥3, m≥4, m≥5, m≥6, and m≥7. In an aspect, $R^a$ and $R^b$ each independently include c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48, 50, 52, 54, 56, or 57, as long as c3<c4. In an aspect, c3 and c4 can be selected from any one of the following integer pairs: c3=1 and c4=50, c3=1 and c4=40, c3=1 and c4=20, c3=1 and c4=16, and c3=1 and c4=10. In an aspect, m=0 and R' and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (or both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. In an aspect, the total number of carbon atoms in linear $R^1$ and $R^2$ is an even number. In an aspect, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. In an aspect, the total number of carbon atoms in the linear $R^1$ and $R^2$ combined is within a range selected from any one of 8 to 96, 8 to 80, 8 to 64, 8 to 48, 8 to 40, 8 to 32, 8 to 28, 8 to 26, 8 to 24, 8 to 22, and 8 to 20.

In an aspect, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. In an aspect, the total number of carbon atoms in $R^1$ and $R^2$ is in a range selected from any one of 8 to 96, 8 to 80, 8 to 64, 8 to 48, 8 to 40, 8 to 32, 8 to 28, 8 to 26, 8 to 24, 8 to 22, and 8 to 20.

In an aspect, $R^1$ and $R^2$ can be identical. In an aspect, $R^1$ and $R^2$ can contain even number of carbon atoms. In an aspect, $R^1$ and $R^2$ can have identical linear alkyl groups. Where $R^1$ and $R^2$ of Formula F-I differ, it is highly desirable that they differ in terms of molar mass thereof by no greater than 145 (or 130, 115, 100, 85, 70, 55, 45, 30, or even 15) grams per mole. In an aspect, in such cases, $R^1$ and $R^2$ differ in terms of total number of carbon atoms contained therein by no greater than 10 (or 9, 8, 7, 6, 5, 4, 3, 2, or even 1).

In an aspect, $R^3$ can be a glycol ether defined by the structural formula:

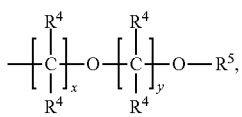

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, and y is a value from about 1 to about 10.

In an aspect, $R^3$ can be a polyglycol ether defined by the structural formula:

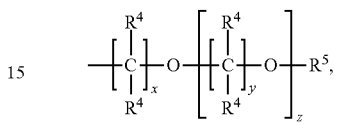

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), is hydrogen or a substituted or unsubstituted alkyl group (C1-. C30), alkenyl group (C1-C30), alkoxy group (C1-C30), aryl group (C4-C30), or arylalkyl group (C5-C30), x is a value from about 0 to about 10, y is a value from about 1 to about 10, and z is a value from about 0 to about 100.

In an aspect, $R^3$ can include up to 60, 50, 40, 30, or 20 carbon atoms. In an aspect, $R^3$ is a C1-C24 group including carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2.

In an aspect, examples of the ester compounds of this disclosure that can be used alone or in combinations in a lubricating oil base stock formulation include 2-(2-(2-hexyloxyethoxy)ethoxy)ethyl 2-methyl-2-octyldecanoate, 2-(2-(2-hexyloxyethoxy)ethoxy)ethyl 2-methyl-2-hexyloctanoate, 2-(2-(3-hexyloxypropoxy)ethoxy)ethyl 2-ethyl-2-octyldecanoate, 2-(3-(2-hexyloxyethoxy)propoxy)ethyl 2-ethyl-2-octyldecanoate, 2-(3-(3-hexyloxypropoxy)propoxy)ethyl 2-ethyl-2-octyldecanoate, 2-(2-(2-butyloxyethoxy)ethoxy)ethyl 2-methyl-2-octyldecanoate, 2-(2-(2-butyloxyethoxy)ethoxy)ethyl 2-methyl-2-hexyloctanoate, 2-(2-(3-butyloxypropoxy)ethoxy)ethyl 2-ethyl-2-octyldecanoate, 2-(3-(2-butyloxyethoxy)propoxy)ethyl 2-ethyl-2-octyldecanoate, 2-(3-(3-butyloxypropoxy)propoxy)ethyl 2-ethyl-2-octyldecanoate, 2-(2-(2-ethoxyethoxy)ethoxy)ethyl 2-methyl-2-octyldecanoate, 2-(2-(2-ethoxyethoxy)ethoxy)ethyl 2-methyl-2-hexyloctanoate, 2-(2-(3-ethoxypropoxy)ethoxy)ethyl 2-ethyl-2-octyldecanoate, 2-(3-(2-ethoxyethoxy)propoxy)ethyl 2-ethyl-2-octyldecanoate, 2-(3-(3-ethoxypropoxy)propoxy)ethyl 2-ethyl-2-octyldecanoate, and the like.

The neo-acid-derived ester compounds of this disclosure can have many applications. One contemplated application is as a base stock of a lubricating oil composition described in detail below. The neo-acid-derived ester compounds of this disclosure can also find use in other fields such as plasticizers, personal care products, heat transfer fluids, hydraulic power transfer oils, processing oils, and the like.

The Lubricating Oil Composition Containing Esters of this Disclosure

General

In this disclosure, a lubricating oil formulation means a lubricating oil product ready for its intended use. Thus, examples of lubricating oil formulations include: engine oils ready for putting into the crankcase of an internal combustion engine; gear oils ready for being dispensed into a gear box; greases ready for being applied to apparatus in need of greasing; and the like. In this disclosure, a lubricating oil composition can be any portion or the entirety of a lubricating oil formulation. Thus, a lubricating oil composition can be, for example: (i) a base stock; (ii) an additive package containing one or more additives; (iii) a mixture of two or more base stocks absent any additive; (iv) a mixture of one or more base stocks with one or more additives but not the entirety of a lubricating oil formulation; and (v) a lubricating oil formulation in its entirety.

The esters of this disclosure are useful as base stocks in formulating lubricating oil compositions. To make a final lubricating oil formulation as a product, one may add additional components, such as other base stocks, additional quantities of the materials already present in the lubricating oil composition, additive components, and the like, to the lubricating oil composition. In an aspect, the lubricating oil composition of this disclosure, can be a lubricating oil formulation.

Lubricating Oil Base Stocks Containing Neo-Acid-Derived Ester

The esters of neo-acids of this disclosure have desirable properties such as KV100, KV40, and viscosity index comparable to certain commercial Group V ester-type base stocks. The high polarity of the neo-acid-derived ester molecules as a result of the presence of the ester group lends them excellent blending capabilities with many other base stocks, providing needed solvency and dispersancy of polar components such as additives and sludge formed during the service life of the lubricating oil. The exceptionally high oxidation stability of the neo-acid-derived ester molecules as a result of the location of the ester group connected to a quaternary carbon atom with no hydrogen directly bonded thereto is particularly desirable for a high-performance lubricating oil formulation which is exposed repeatedly to oxidative environment such as automotive engine oils.

The lubricating oil base stock of this disclosure can comprise a single neo-acid-derived ester compound as disclosed above. The concentration of the ester compound in the base stock can be, e.g., at least 80, 90, 95, 98, or even 99 wt %, based on the total weight of the base stock.

The lubricating oil base stock of this disclosure can comprise two or more neo-acid-derived esters as disclosed above. Such base stock can be produced by mixing two ester compounds in their substantially pure form, or produced from a single esterification reaction operation by reacting (i) one neo-acid with two or more alcohols or (ii) two or more neo-acids with one or more alcohols. Such mixed-ester base stock can be particularly advantageous where a mixture of neo-acids (including neo-acids with similar molecular weights and/or molecular structures) or a mixture of alcohols (including alcohols with similar molecular weights and/or molecular structures) can be procured at a lower cost than a pure single-compound neo-acid product or alcohol product.

The lubricating oil base stock of the present disclosure desirably has a KV100 in the range from k1 to k2 cSt, where k1 and k2 can be, independently, 1.0, 1.2, 1.4, 1.5, 1.6, 1.8, 2.0, 2.2, 2.4, 2.5, 2.6, 2.8, 3.0, 3.2, 3.4, 3.5, 3.6, 3.8, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, as long as k1<k2. In an aspect, k1=4.0, and k2=30.0. In another aspect, k1=5.0, and k2=25.0. Therefore, the base stock of the present disclosure has a relatively "low" viscosity at the normal operating temperature of an internal combustion engine lubricating oil.

The lubricating oil base stock of the present disclosure may have a viscosity index as determined pursuant to ASTM D2270 in the range from v1 to v2, where v1 and v2 can be, independently, −100, −90, −80, −70, −60, −50, −40, −30, −20, −10, 0, 10, 20, 30, 40, 50, 60, 70, 80, 90, 100, 110, 120, 130, 140, 150, 160, 170, 180, 190, 200, 210, 220, 230, 240, 250, 260, 270, 290, or 300, as long as v1<v2. In an aspect, v1 and v2 can be a pair of values selected from any one of v1=0 and v2=250, v1=25 and v2=200, and v1=100 and v2=170.

The base stock of the present disclosure may have a NV value in the range from n1 to n2 wt %, where n1 and n2 can be, independently, 0, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, or 90, as long as n1<n2. In an aspect, n1 and n2 can be a pair of values selected from any one of n1=0 and n2=50, n1=0 and n2=30, n1=0 and n2=20, and n1=0 and n2=16. In general, for the same type of neo-acid-derived ester base stock, the larger the molecular weight of the molecule, the lower the NV value. For engine oils and base stocks containing a neo-acid-derived ester, NV values can be lower than comparative engine oil and base stock formulations.

The base stock of this disclosure desirably have an aniline value as determined by ASTM D611 of no higher than 30, 25, 20, or 15.

Neo-acid-derived esters are demonstrated as good quality lubricating oil base stocks. In a surprising manner, it has been found that selective base stocks of this disclosure based on neo-acid-derived esters perform better than gamma-branched alcohols-derived ester base stocks having at the same molecular weight and with comparable molecular structure. In particular, it has been found that selective ester base stocks of this disclosure tend to have significantly higher oxidation stability compared to gamma-alcohol-derived esters having the same molecular weight and/or similar KV100.

Moreover, compared to PAO base stocks at similar viscosity (KV100, in particular), the base stock of this disclosure containing a neo-acid-derived ester tend to have higher polarity and lower volatility (NV value, in particular).

The neo-acid-derived ester base stock of this disclosure can be used as a primary base stock or a co-base stock in any lubricating oil formulation. In an aspect, the neo-acid-derived ester base stock of this disclosure is used as a co-base stock in conjunction with a second base stock designated as a primary base stock. In certain applications, it may be desirable to include two or even more additional base stocks in the lubricating oil formulation, in addition to the neo-acid-derived ester base stock of this disclosure. For the convenience of description, the neo-acid-derived ester base stock is merely referred to as a generic base stock herein, regardless of its primary base stock or co-base stock designation. The base stock of this disclosure containing a neo-acid-derived ester can be particularly advantageous when used as a co-base stock with a non-polar base stock such as those Group I, II, III, GTL, and Group IV base stocks.

The neo-acid-derived ester base stocks of this disclosure can be used for formulating automobile engine lubricating oils, including those meeting the SAE J300 classification standards. However, it is contemplated that the base stocks of this disclosure may be used to formulate other lubricating oils (e.g., automobile drive-line oils, industrial lubricating oils, gear oils, greases, and the like), heat transfer oils (e.g., transformer oils), hydraulic power transfer oils, processing oils, and the like.

The neo-acid-derived ester base stock can be present in the lubricating oil formulation of this disclosure in an amount from about c1 to c2 wt %, based on the total weight of the lubricating oil composition, where c1 and c2 can be, independently, 1, 2, 3, 4, 5, 6, 7, 8, 9, 10, 15, 20, 25, 30, 35, 40, 45, 50, 55, 60, 65, 70, 75, 80, 85, 90, or 95, as long as c1<c2. In an aspect, c1 and c2 can be range limits selected from any one of c1=3 and c2=50, and c1=5 and c2=30. In general, it is desirable that the lubricating oil composition contains the neo-acid-derived ester base stock as a co-base stock. However, it is also contemplated that the lubricating oil formulation of this disclosure may contain the neo-acid derived ester base stock as a primary base stock, and in an extreme case, the lubricating oil formulation may consist essentially of a neo-acid derived ester base stock and additives.

Owing to the high polarity of the neo-acid-derived ester base stocks resulting from the ester group in their molecular structures, the lubricating oil compositions of this disclosure can have an improved additive and sludge solvency and dispersancy compared to other lubricating oil compositions free of ester-type base stocks. In addition, a lubricating oil composition including a neo-acid-derived ester base stock can have improved seal compatibility compared to compositions free of ester-type base stocks.

Other Base Stocks Useful in the Lubricating Oil Compositions

A wide range of lubricating oil base stocks known in the art can be used in conjunction with the neo-acid-derived ester base stock in the lubricating oil compositions of this disclosure, as a primary base stock or a co-base stock. Such other base stocks can be either derived from natural resources or synthetic, including un-refined, refined, or re-refined oils. Un-refined oil base stocks include shale oil obtained directly from retorting operations, petroleum oil obtained directly from primary distillation, and ester oil obtained directly from a natural source (such as plant matters and animal tissues) or directly from a chemical esterification process. Refined oil base stocks are those un-refined base stocks further subjected to one or more purification steps such as solvent extraction, secondary distillation, acid extraction, base extraction, filtration, and percolation to improve the at least one lubricating oil property. Re-refined oil base stocks are obtained by processes analogous to refined oils but using an oil that has been previously used as a feed stock.

API Groups I, II, III, IV and V are broad categories of base stocks developed and defined by the American Petroleum Institute (API Publication 1509; www.API.org) to create guidelines for lubricating oil base stocks. Group I base stocks generally have a viscosity index of from about 80 to 120 and contain greater than about 0.03% sulfur and less than about 90% saturates. Group II base stocks generally have a viscosity index of from about 80 to 120, and contain less than or equal to about 0.03% sulfur and greater than or equal to about 90% saturates. Group III base stocks generally have a viscosity index greater than about 120 and contains less than or equal to about 0.03% sulfur and greater than about 90% saturates. Group IV includes polyalpha-olefins (PAO). Group V base stocks include base stocks not included in Groups I-IV. The table below summarizes properties of each of these five groups.

| Base Stock Properties | | | |
|---|---|---|---|
| | Saturates | Sulfur | Viscosity Index |
| Group I | Higher than 90 and/or | Higher than 0.03% and | At least 80 and at most 120 |
| Group II | Higher than 90 and | At most 0.03% and | At least 80 and at most 120 |
| Group III | At least 90 and | At most 0.03% and | At least 120 |
| Group IV | PAO products | | |
| Group V | All other products not included in Groups I, II, III, and IV | | |

Natural oils include animal oils (e.g., lard), vegetable oils (e.g., castor oil), and mineral oils. Animal and vegetable oils possessing favorable thermal oxidation stability can be used. Mineral oils vary widely as to their crude source, e.g., as to whether they are paraffinic, naphthenic, or mixed paraffinic-naphthenic. Oils derived from coal or shale are also useful in this disclosure. Natural oils vary also as to the method used for their production and purification, e.g., their distillation range and whether they are straight run or cracked, hydrorefined, or solvent extracted.

Group II and/or Group III base stocks are generally hydroprocessed or hydrocracked base stocks derived from crude oil refining processes.

Synthetic base stocks include polymerized and interpolymerized olefins (e.g., polybutylenes, polypropylenes, propylene isobutylene copolymers, ethylene-olefin copolymers, and ethylene-alphaolefin copolymers).

Synthetic polyalpha-olefins ("PAO") base stocks are placed into Group IV. Advantageous Group IV base stocks are those made from one or more of C6, C8, C10, C12, and C14 linear alpha-olefins ("LAO"s). These base stocks can be commercially available at a wide range of viscosity, such as a KV100 in the range from 1.0 to 1,000 cSt. The PAO base stocks can be made by polymerization of the LAO(s) in the presence of Lewis-acid type catalyst or a metallocene compound-based catalyst system. High quality Group IV PAO commercial base stocks include the SpectraSyn™ and SpectraSyn Elite™ series available from ExxonMobil Chemical Company having an address at 4500 Bayway Drive, Baytown, Tex. 77520, United States.

All other synthetic base stocks, including but not limited to alkyl aromatics and synthetic esters are in Group V.

Additional esters not in the neo-acid-derived ester category in a minor amount may be useful in the lubricating oil compositions of this disclosure. Additive solvency and seal compatibility characteristics may be further imparted by the use of esters such as the esters of dibasic acids with monoalkanols and the polyol esters of monocarboxylic acids. Esters of the former type include, e.g., the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc. Useful ester-type Group V base stock include the Esterex™ series commercially available from ExxonMobil Chemical Company.

One or more of the following maybe used as a base stock in the lubricating oil of this disclosure as well: (1) one or more Gas-to-Liquids (GTL) materials; and (2) hydrodewaxed, hydroisomerized, solvent dewaxed, or catalytically dewaxed base stocks derived from synthetic wax, natural wax, waxy feeds, slack waxes, gas oils, waxy fuels, hydrocracker bottoms, waxy raffinate, hydrocrackate, thermal crackates, foots oil, and waxy materials derived from coal liquefaction or shale oil. Such waxy feeds can be derived from mineral oils or non-mineral oil processing or can be synthetic (e.g., Fischer-Tropsch feed stocks). Such base stocks can include linear or branched hydrocarbyl compounds of C20 or higher, including C30 or higher.

The present lubricating oil compositions include one or more Group I, II, III, IV, or V base stocks in addition to the neo-acid-derived ester base stock. In an aspect, Group I base stocks, if any, are present at a relatively low concentration if a high quality lubricating oil is desired. Group I base stocks may be introduced as a diluent of an additive package at a small quantity. Groups II and III base stocks can be included in the lubricating oil compositions of this disclosure, including those with high quality, e.g., those having a VI from 100 to 120. Group IV and V base stocks, including those of high quality, are also included into the lubricating oil compositions of this disclosure.

Lubricating Oil Additives

The present lubricating oil composition can also contain one or more of the commonly used lubricating oil performance additives including but not limited to dispersants, detergents, viscosity modifiers, antiwear additives, corrosion inhibitors, rust inhibitors, metal deactivators, extreme pressure additives, anti-seizure agents, wax modifiers, viscosity modifiers, fluid-loss additives, seal compatibility agents, lubricity agents, anti-staining agents, chromophoric agents, defoamants, demulsifiers, densifiers, wetting agents, gelling agents, tackiness agents, colorants, and others. For a review of many commonly used additives and the quantities used, see: (i) Klamann in Lubricants and Related Products, Verlag Chemie, Deerfield Beach, Fla.; ISBN 0-89573-177-0; (ii) "Lubricant Additives," M. W. Ranney, published by Noyes Data Corporation of Parkridge, N J (1973); (iii) "Synthetics, Mineral Oils, and Bio-Based Lubricants," Edited by L. R. Rudnick, CRC Taylor and Francis, 2006, ISBN 1-57444-723-8; (iv) "Lubrication Fundamentals", J. G. Wills, Marcel Dekker Inc., (New York, 1980); (v) Synthetic Lubricants and High-Performance Functional Fluids, 2nd Ed., Rudnick and Shubkin, Marcel Dekker Inc., (New York, 1999); and (vi) "Polyalpha-olefins," L. R. Rudnick, Chemical Industries (Boca Raton, Fla., United States) (2006), 111 (Synthetics, Mineral Oils, and Bio-Based Lubricants), 3-36. Reference is also made to: (a) U.S. Pat. No. 7,704,930 B2; (b) U.S. Pat. No. 9,458,403 B2, Column 18, line 46 to Column 39, line 68; (c) U.S. Pat. No. 9,422,497 B2, Column 34, line 4 to Column 40, line 55; and (d) U.S. Pat. No. 8,048,833 B2, Column 17, line 48 to Column 27, line 12, the disclosures of which are incorporated herein in their entirety. These additives are commonly delivered with varying amounts of diluent oil that may range from 5 wt % to 50 wt % based on the total weight of the additive package before incorporation into the formulated oil. The additives useful in this disclosure do not have to be soluble in the lubricating oil compositions. Insoluble additives in oil can be dispersed in the lubricating oil compositions of this disclosure.

When lubricating oil compositions contain one or more of the additives discussed above, the additive(s) are blended into the lubricating oil composition in an amount sufficient for it to perform its intended function.

It is noted that many of the additives are shipped from the additive manufacturer as a concentrate, containing one or more additives together, with a certain amount of base oil diluents.

Methods for Making the Ester Products Containing Neo-Acid Ester Compounds and Lubricating Oil Base Stock Containing the Same Provided herein are methods for making an ester product comprising a compound of the structural Formula I and/or a lubricating oil base stock comprising the compound of the structural Formula F-I as follows:

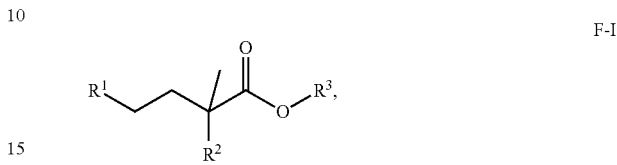

wherein: $R^1$ and $R^2$ are each independently a hydrocarbyl group containing at least two (2) carbon atoms (such as a C2-C60 hydrocarbyl group, a C2-C60 alkyl group, a C2-C60 linear or branched alkyl group, or a C2 to C30 linear or branched alkyl group; $R^3$ is glycol ether or a polyglycol ether. The present methods comprise the step of reacting a neo-acid of the structural Formula F-II and/or an anhydride thereof with an alcohol of the structural Formula F-III in the presence of an acid catalyst to obtain a reaction mixture. The compounds of the structural Formula F-II is defined as:

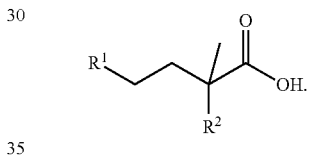

where $R^1$, and $R^2$ correspond to the substitutents $R^1$, and $R^2$ of the Formula F-I, respectively. A compound of the structural Formula F-III is defined by the structural formula $R^3$—OH where the $R^3$ substituent corresponds to $R^3$ substituent of the Formula F-I. The method further comprises the step of obtaining the ester product or the lubricating oil base stock from the reaction mixture.

It is highly desirable that the acid/anhydride used in the reaction are those of a single mono-acid for the purpose of making a single compound of the Formula F-I, an ester product (such as a lubricating oil base stock) containing one or more compound(s) having formula (I), although those of multiple acids can be used as well, especially for the purpose of making an ester product or a lubricating oil base stock which can comprise a mixture of multiple, different compounds each of the structural Formula F-I.

In the structural Formula F-I, $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48 50, 52, 54, 56, 58, or 60, as long as c1<c2. In an aspect, c1 and c2 may define a range selected from any one of c1=2 and c2=30, c1=2 and c2=24, and c1=4 and c2=16. In an aspect, $R^1$ and $R^2$ each independently contain even number of carbon atoms.

At least one of $R^1$ and $R^2$ (or both $R^1$ and $R^2$ independently each) can be a branched alkyl group, such as a branched alkyl group of the structural Formula F-IV as follows:

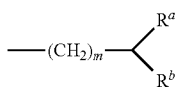

where $R^a$ and $R^b$ are independently hydrocarbyl groups, alkyl groups, linear or branched alkyl groups, or linear alkyl groups, m is a non-negative integer, including an integer satisfying an inequality selected from a group of m≥2, m≥3, m≥4 m≥5, m≥6, and m≥7. $R^a$ and $R^b$ can include, independently, c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48 50, 52, 54, 56, or 57, as long as c3<c4. In an aspect, c3 and c5 may be a pair of values selected from any one of c3=1 and c4=50, c3=1 and c4=40, c3=1 and c4=20, c3=1 and c4=16, and c3=1, and c4=10. In an aspect, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (or both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. In an aspect, the total number of carbon atoms in linear $R^1$ and $R^2$ is an even number. In an aspect, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. In an aspect, the total number of carbon atoms in the linear $R^1$ and $R^2$ combined is within a range selected from any one of 8 to 96, 8 to 80, 8 to 64, still more 8 to 48, 8 to 40, 8 to 32, 8 to 28, 8 to 26, 8 to 24, 8 to 22, and 8 to 20.

In an aspect, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. In an aspect, the total number of carbon atoms in $R^1$ and $R^2$ is in a range selected from any one of 8 to 96, more 8 to 80, 8 to 64, 8 to 48, 8 to 40, 8 to 32, 8 to 28, 8 to 26, 8 to 24, 8 to 22, and 8 to 20.

In an aspect, $R^1$ and $R^2$ are identical. In such case, $R^1$ and $R^2$ can contain even number of carbon atoms. In an aspect, $R^1$ and $R^2$ are identical linear alkyl groups. Where $R^1$ and $R^2$ differ, the groups can differ in terms of molar mass thereof by a gram per mole value less than any range endpoint selected from a group of 145, 130, 115, 100, 85, 70, 55, 45, 30, and 15. In an aspect, $R^1$ and $R^2$ can differ in terms of total number of carbon atoms contained therein by less than a range endpoint selected from a group of 10, 9, 8, 7, 6, 5, 4, 3, 2, and 1.

In an aspect, $R^3$ can be a glycol ether having a structure corresponding to the following formula:

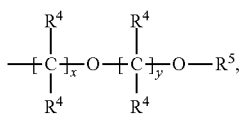

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, and y is a value from about 1 to about 10.

In an aspect, $R^3$ can be a polyglycol ether having a structure corresponding to the following formula:

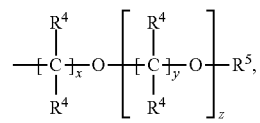

where each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from about 0 to about 10, y is a value from about 1 to about 10, and z is a value from about 0 to about 100.

In an aspect, $R^3$ can include up to 60, 50, 40, 30, or 20 carbon atoms. In an aspect, $R^3$ is a C1-C24 group including carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2.

The neo-acid product useful in methods for making the present ester products can be made by: (a) providing a vinylidene olefin feed containing a vinylidene olefin defined by the structural Formula F-V:

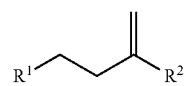

where $R^1$ and $R^2$ correspond to the $R^1$ and $R^2$ in Formula F-I; (b) contacting the vinylidene olefin with carbon monoxide in a reactor in the presence of an acid catalyst (such as at a carbon monoxide partial pressure is at least one selected from a group of 1.0 MPa, 3.5 MPa, and 5.0 MPa) to obtain a reaction mixture; (c) contacting the reaction mixture with water to obtain an acid product mixture; and (d) obtaining at least a portion of the neo-acid product from the crude acid mixture. The vinylidene olefin feed useful in step (a) above can be advantageously made from a terminal olefin monomer feed in a process containing the following steps: providing a monomer feed containing a terminal olefin defined by the structural Formula F-VI as follows: $R^1$—CH=CH$_2$ (F-VI) and a terminal olefin defined by the structural Formula F-VII as follows: $R^2$—CH=CH$_2$ (F-VII), where $R^1$ and $R^2$ correspond to the $R^1$ and $R^2$ of structural Formulas F-I, F-II and F-V, respectively; oligomerizing the monomer feed in an oligomerization reactor in the presence of a catalyst system containing a metallocene compound to obtain an oligomerization product mixture; and obtaining at least a portion of the vinylidene olefin feed from the oligomerization product mixture. In this method, where $R^1$ and $R^2$ of the Formula F-I are identical, a single terminal olefin of the Formula F-VI is used in the monomer feed. Where $R^1$ and $R^2$ of the Formula F-I of the neo-alcohol are different, at least two terminal olefins having different Formulas F-VI and F-VII are used in the monomer feed.

In case two different terminal olefins are used, in the monomer feed, the oligomerization product mixture obtained can comprise up to four vinylidene olefins as dimers of the two terminal olefins, which may be separated to obtain the desirable vinylidene olefin feed containing one, two, three, or all four vinylidene olefins. Nine vinylidene olefin dimers can result from three different terminal olefins in the monomer feed. These different vinylidene olefins, if contained in the vinylidene olefin feed of the present methods of making the neo-acid described above, can be converted into corresponding neo-acids in the neo-acid product, which, in turn, can be converted into corresponding ester compounds in the neo-acid-derived ester product.

The above processes for making neo-acid product starting from terminal olefin monomer via the vinylidene olefin intermediate can be illustrated in the following Scheme-I:

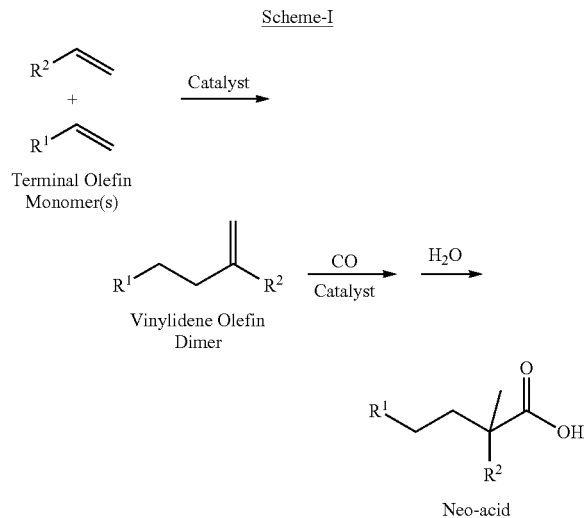

Only one type of vinylidene olefin dimer is illustrated in Scheme-I above. Specific examples of Scheme-I is provided in Part A of the Examples in this disclosure Co-pending, co-assigned U.S. Provisional Patent Application No. 62/551,081 (entitled "Process for Making Vinylidene Olefin" and having a filing date of Aug. 28, 2017) discloses vinylidene olefin dimers of terminal olefins useful for making neo-acids suitable for making neo-alcohols of this disclosure and processes for making such vinylidene dimers, the content of which is incorporated herein by reference in its entirety.

Non-limiting examples of neo-acids useful in the process of this disclosure include the following: 2-ethyl-2-methylhexanoic acid; 2-methyl-2-propylheptanoic acid; 2-butyl-2-methyloctanoic acid; 2-methyl-2-pentylnonanoic acid; 2-hexyl-2-methyldecanoic acid; 2-heptyl-2-methylundecanoic acid; 2-methyl-2-octyldodecanoic acid; 2-decyl-2-methyltetradecanoic acid; 2-dodecyl-2-methylhexadecanoic acid; 2-methyl-2-tetradecyloctadecanoic acid; and 2-methyl-2-hexadecylicosanoic acid.

Co-pending, co-assigned U.S. Provisional Application Ser. No. 62/565,560 filed Sep. 29, 2017 (2017EM311) discloses neo-acids suitable for use in the process of this disclosure for making neo-acid-derived esters and processes for making neo-acids, the content of which is incorporated herein by reference in its entirety.

The anhydrides of the neo-acid can be prepared from a corresponding neo-acid of Formula F-II by, e.g., dehydration. Dehydration can be achieved by, e.g., reacting with dehydration agents such as $P_2O_5$, followed by separation.

In the method for making the ester of this disclosure, either the neo-acid of Formula F-II, or its anhydride, or a mixture thereof, can be used to react with the alcohol of Formula F-III. In the alcohol of Formula F-III, $R^3$ corresponds to the $R^3$ of Formula F-I as described herein.

Particularly, desirable examples of the alcohol useful in the process of this disclosure include glycol ethers alcohols such as methoxyethanol, ethoxyethanol, propoxyethanol, butoxyethanol, pentoxyethanol, hexyloxyethanol, phenoxyethanol, diethylene glycol methyl ether, diethylene glycol ethyl ether, diethylene glycol propyl ether, diethylene glycol butyl ether, diethylene glycol pentyl ether, diethylene glycol hexyl ether, diethylene glycol benzyl ether, triethylene glycol methyl ether, triethylene glycol ethyl ether, triethylene glycol propyl ether, triethylene glycol butyl ether, triethylene glycol pentyl ether, triethylene glycol hexyl ether, triethylene glycol benzyl ether, tetraethylene glycol methyl ether, tetraethylene glycol ethyl ether, tetraethylene glycol propyl ether, tetraethylene glycol butyl ether, tetraethylene glycol pentyl ether, tetraethylene glycol hexyl ether, tetraethylene glycol benzyl ether, propylene glycol methyl ether, propylene glycol ethyl ether, propylene glycol propyl ether, propylene glycol butyl ether, propylene glycol hexyl ether, propylene glycol benzyl ether, dipropylene glycol methyl ether, dipropylene glycol propyl ether, dipropylene glycol butyl ether, dipropylene glycol pentyl ether, dipropylene glycol hexyl ether, dipropylene glycol benzyl ether, and the like.

In an aspect, a single alcohol of Formula F-III can be used in the esterification reaction to produce a single ester of this disclosure and/or a lubricating oil base stock containing a single ester compound of this disclosure. In such case, if an acid/anhydride of a single mono-acid is used, a high-purity ester compound of Formula F-I can be obtained and used as a lubricating oil base stock. This is illustrated in Examples B1, B2, and B3 in this disclosure.

It is also contemplated that multiple alcohols can be used in the esterification reaction. In the case where two different alcohols and the acid/anhydride of a single mono-acid are used in the reaction, the reaction mixture will comprise two different ester compounds. The ratio between the quantities of two ester compounds can change as a function of the ratio between the quantities of the two alcohols used. In certain situations, such as when a mixture of alcohols having similar molecular weights and structures can be procured at a lower cost than a pure alcohol compound, this embodiment can be highly economic to produce a mixture of ester compounds with similar molecular structures, molecular weights, and properties suitable as a lubricating oil base stock product.

The catalyst used in the reaction can be an acid, desirably a strong acid. Non-limiting examples of such acid are: p-toluenesulfonic acid monohydride (PTSA), titanium isopropoxide and sulfuric acid.

The reaction can be advantageously carried out in the presence of a solvent. The specific solvent used is not critical as long as it is inert in the reaction. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof;

n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

The reaction mixture from the esterification reaction typically comprises the intended ester product(s), water, and one or more of unreacted acid/anhydride and alcohol, and byproducts such as ethers and esters of the acid catalyst. Continuous removal of water from the reaction system can result in higher yield of the ester product. Components in the reaction mixture having a boiling point lower than the intended neo-acid-derived ester can be removed by flashing. Depending on the reactants used and reaction conditions, purification methods such as solvent extraction, chromatography, distillation, and the use of sorbents can be carried out to remove byproducts from reaction mixture to finally obtain an ester product of this disclosure containing a single compound of Formula F-II or a mixture of multiple compounds of Formula F-I which can be used as a base stock product, or combined with other, similar compounds to form a base stock product. In an aspect, the neo-acid ester product obtainable from the process of this disclosure consists essentially of one or more neo-acid-derived ester compounds. In an aspect, the neo-acid ester product obtainable from the process of this disclosure comprises neo-acid-derived ester compounds at a total concentration thereof, based on the total weight of the neo-acid ester product, at least 95 wt %, or at least 98 wt %, or even at least 99 wt %. In an aspect, the neo-acid ester product obtainable from the process of this disclosure consists essentially of one predominant neo-acid-derived ester compound. In an aspect, the neo-acid ester product obtainable from the process of this disclosure comprises a predominant neo-acid-derived ester compound at a concentration thereof, based on the total weight of the neo-acid ester product, of at least 95 wt %, or at least 98 wt %, or even at least 99 wt %.

This disclosure is further illustrated by the following non-limiting examples.

EXAMPLES

In the following examples, kinematic viscosity at 100° C. ("KV100") and 40° C. ("KV40") of fluids were determined pursuant to ASTM standards D-445; viscosity index ("VI") was determined pursuant to ASTM standard D-2270; and Noack volatility ("NV") were determined using thermal gravimetric analysis ("TGA").

Synthesis of Novel Compounds

By changing the glycol ether component of the neo-acid-derived esters in accordance with the present disclosure, the overall polarity of fluids treated with such compounds can be modified. For example, the polarity of a neo-acid-derived ester may be modified by varying the $R^3$ glycol ether group of Formula F-I with any number of synthetic and/or commercially available glycol ethers. For example, glycol ethers such as di(ethylene glycol) monohexyl ether, tri(ethylene glycol) monomethyl ether, tri(propylene glycol) monomethyl ether, tri(ethylene glycol) monoethyl ether, tri(ethylene glycol) monobutyl ether, di(ethylene glycol) monoethyl ether, di(ethylene glycol) monobutyl ether, tri(propylene glycol) monopropyl ether, tri(propylene glycol) monobutyl ether, poly(ethylene glycol) dodecyl ether (Brij 30), and ethylene glycol mono-2-ethylhexyl ether can be used. Glycol ethers, having both ether and alcohol functional groups in the same molecule, represent a versatile class of organic solvents. The Dow Chemical Company manufactures this glycol ether in large quantities. DOW glycol ether products are produced through continuous processes of selectively reacting an alcohol (ethanol, butanol, hexanol) with ethylene oxide. Diethylene glycol monohexyl ether ($C_6H_{13}$(OCH$_2$CH$_2$)$_2$OH, Hexyl CARBITOL Solvent) displays a strong hydrocarbon-type solvency.

Example 1

Synthesis of 2-(2-(2-hexyloxyethoxy)ethoxy)ethyl 2-methyl-2-octyldecanoate

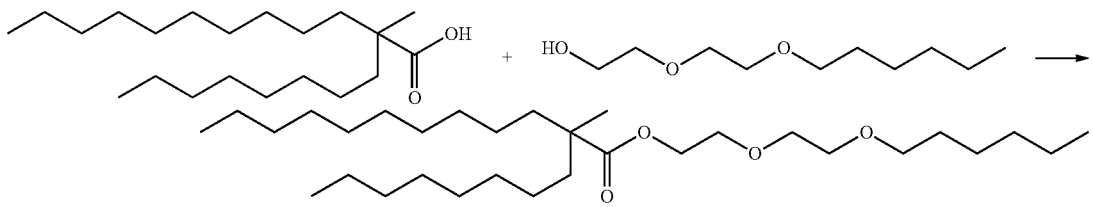

2-methyl-2-octyldodecanoic acid (7 g, 0.0215 mol, MW 326.17), diethylene glycol hexyl ether (8.2 g 0.043 mol, MW 190.28) and p-toluenesulfonic acid monohydride (PTSA) (2.04 g, 0.0108 mol, MW 190.22) were mixed with 75 mL toluene in three necked round bottom flask along with a dean-stark apparatus. The solution was reflux for overnight (18 h). In 18 hours, ~2-3 mL water was collected in the trap. Toluene was removed by simple distillation at 50° C. under vacuum. The extracted product in methylene chloride washed with water (1×100 mL) and saturated NaHCO$_3$ (1×100 mL). Evaporated the methylene chloride and followed by flash chromatography with hexane. The hexane layer is removed by roto-vap at 60° C. under vacuum and high boiling components by air bath oven at 190° C. The isolated product was characterized by IR, $^1$H NMR, $^{13}$CNMR. Yields: 7.5 g (70%). IR (cm$^{-1}$): 0.2925, 2855, 1731, 1467 1379 1134, and 722. $^{13}$C NMR (CDCl$_3$): 177.91, 71.63, 70.59, 70.11, 69.26, 63.28, 45.92, 39.39, 31.92, 31.089, 31.70, 30.20, 29.66, 29.63, 29.61, 29.56, 29.50, 29.34, 29.31, 25.77, 24.53, 22.67, 22.62, 21.16, and 14.10.

Example 2

Synthesis of 2-(2-(2-butoxyethoxy)ethoxy)ethyl 2-methyl-2-octyldecanoate

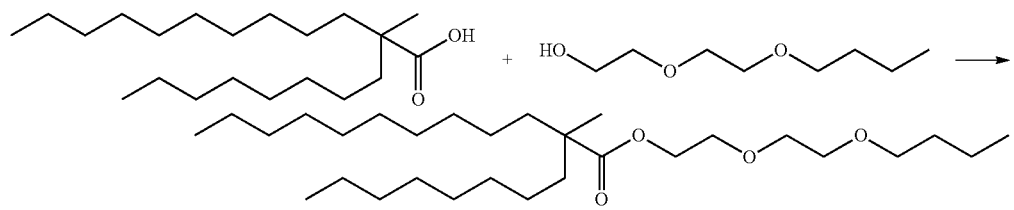

2-methyl-2-octyldodecanoic acid (7 g, 0.0215 mol, MW 326.17), diethylene glycol butyl ether (6.97 g 0.043 mol, MW 162.23) and p-toluenesulfonic acid monohydride (PTSA) (2.04 g, 0.0108 mol, MW 190.22) were mixed 75 mL toluene in three necked round bottom flask along with a dean-stark apparatus. Then solution was reflux for overnight (18 h). In 18 hours, ~2-3 mL water was collected in the trap. Toluene was removed by simple distillation at 50° C. The extracted product in methylene chloride was washed with water (1×100 mL) and saturated NaHCO$_3$ (1×100 mL). Evaporated in methylene chloride and followed by flash chromatography with hexane. The hexane layer was removed by roto-vap at 60° C. under vacuum and high boiling components by air bath oven at 180° C. The isolated product was characterized by IR, $^1$H NMR, $^{13}$CNMR. Yields: 6.0 g (60%). IR (cm$^{-1}$): 2955, 2925, 2854, 731, 1466, 1373, 1131, and 721.47. $^{13}$C NMR (CDCl$_3$): 140.59, 71.27, 70.60, 70.14, 69.27, 63.26, 46.00, 39.61, 31.90, 31.86, 31.72, 30.18, 29.65, 29.62, 29.54, 29.49, 29.35, 29.30, 24.51, 22.67, 31.12, 19.26, 14.10, and 13.89.

Example 3

Synthesis of 2-(2-(2-ethoxyethoxy)ethoxy)ethyl 2-methyl-2-octyldecanoate

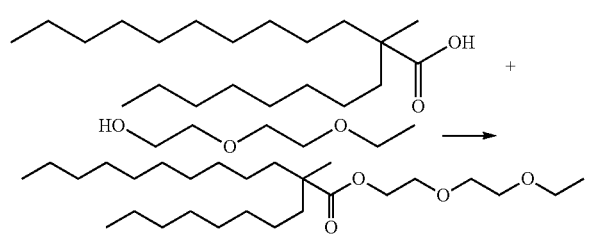

2-methyl-2-octyldodecanoic acid (7 g, 0.0215 mol, MW 326.17), diethylene glycol ethyl ether (5.8 g 0.043 mol, MW 134.18) and p-toluenesulfonic acid monohydride (PTSA) (2.04 g, 0.0108 mol, MW 190.22) were mixed 75 mL toluene in three necked round bottom flask along with a dean-stark apparatus. Then solution was reflux for overnight (18 h). In 18 hours, ~2 mL water was collected in the trap. Toluene was removed by simple distillation at 50° C. The extracted product in methylene chloride was washed with water (1×100 mL) and saturated NaHCO$_3$ (1×100 mL). Evaporated the methylene chloride and followed by flash chromatography with hexane. The hexane layer was removed by roto-vap at 60° C. under vacuum and high boiling components by air bath oven at 180° C. The isolated product was characterized by IR, $^1$H NMR, $^{13}$CNMR. Yields: 6.0 g (60%). IR (cm$^{-1}$): 0.2954, 2924, 2854, 1731, 1467, 1378, 1131, and 721. $^{13}$C NMR (CDCl$_3$): 177.44, 70.54, 69.82, 69.20, 66.62, 63.14, 45.86, 39.35, 31.87, 31.83, 30.14, 29.59, 29.58, 29.49, 29.45, 29.29, 29.26, 24.47, 22.61, 21.07, 15.07, and 14.02.

Example 4

Lube Properties of Base Stocks

The kinematic viscosity (Kv) of the liquid product was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The products were evaluated as synthetic base stocks.

The ester fluids were evaluated as synthetic basestocks and results are shown in Table 2.

TABLE 2

| Example # | MW | Kv$_{100}$ cSt | Kv$_{40}$ cSt | VI | Noack (TGA) |
|---|---|---|---|---|---|
| 1 | 498 | 6.77 | 36.7 | 142 | 10.3 |
| 2 | 470 | 3.60 | 13.1 | 171 | 14.7 |
| 3 | 442 | 3.36 | 13.7 | 118 | 18.0 |

Example 5

Heat Capacity of Base Stocks

In addition to lubrication applications, base stock fluids and circulating fluids can also function to transfer heat from high temperature zones. In lubricated systems, examples of heat sources that are often controlled by cooling systems include: heat generated by combustion processes, heat resulting from friction within a lubricated contact, heat created by energy sources, and heat used in manufacturing processes (e.g., paper and steel making).

In some cases, specialized fluids are used for the sole purpose of removing heat from high temperature zones. Examples include coolants used in internal combustion engine applications, and transformer oils used to cool electrical distribution equipment. Formulations containing glycol ether esters of neo-acids in accordance with the present disclosure can also meet the requirements for cooling systems used to cool battery and power generation systems in electric and hybrid vehicles to dissipate and distribute heat.

Base stock fluids in accordance with the present disclosure formulated as lubricating and/or cooling fluids can remove heat via combinations of conductivity and convection mechanisms. The heat removed can be a function of:

fluid properties, such as heat capacity and thermal conductivity; system design, such as selection of materials that determine the heat flow across fluid/surface interfaces; and operational factors, such as fluid flow rate and temperature difference between fluid and the high temperature zone requiring cooling.

In this example the specific heat capacity of the samples was measured and evaluated against a comparative commercial base stock formulation. Results are shown in Table 3.

TABLE 3

Specific Heat Capacity (J/g/° C.) of Base Stocks

| Temp (° C.) | Example 1 | Example 2 | Example 3 | Comparative 1 |
|---|---|---|---|---|
| 20 | 2.01 | 1.94 | 1.98 | 1.46 |
| 40 | 2.07 | 1.99 | 2.03 | 1.52 |
| 60 | 2.14 | 2.04 | 2.09 | 1.57 |

The invention claimed is:

1. A compound of structural Formula F-I:

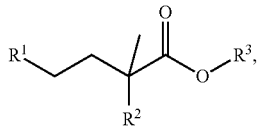

wherein $R^1$ and $R^2$ are independently each a hydrocarbyl group comprising at least two carbon atoms; and $R^3$ is a glycol ether or a polyglycol ether.

2. The compound of claim 1, wherein $R^1$ and $R^2$ are each independently a C2 to C30 linear or branched alkyl group.

3. The compound of claim 1, wherein at least one of $R^1$ and $R^2$ is a linear alkyl group.

4. The compound of claim 3, wherein at least one of $R^1$ and $R^2$ is selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

5. The compound of claim 4, wherein at least one of $R^1$ and $R^2$ is selected from n-butyl, n-hexyl, n-octyl, n-decyl, and n-dodecyl.

6. The compound of claim 1, wherein $R^1$ and $R^2$ are each independently a branched alkyl group selected from 2-ethylhexyl, 2-propylheptanyl, 2-butyloctyl and 3,5-dimethyloctyl.

7. The compound of claim 1, wherein $R^1$ and $R^2$ are identical.

8. The compound claim 1, wherein $R^3$ is a glycol ether of the structural formula:

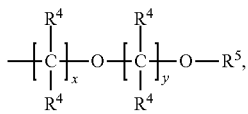

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from 0 to 10, and y is a value from 1 to 10.

9. The compound of claim 8, wherein $R^3$ comprises 2 to 24 carbon atoms.

10. The compound of claim 1, wherein $R^3$ is a polyglycol ether of the structural formula:

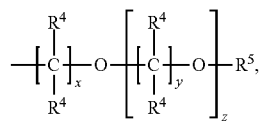

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from 0 to 10, y is a value from 1 to 10, and z is a value from 0 to 100.

11. The compound of claim 1, wherein $R^3$ is one or more selected from a group of methoxyethanol, ethoxyethanol, propoxyethanol, butoxyethanol, pentoxyethanol, hexyloxyethanol, phenoxyethanol, diethylene glycol methyl ether, diethylene glycol ethyl ether, diethylene glycol propyl ether, diethylene glycol butyl ether, diethylene glycol pentyl ether, diethylene glycol hexyl ether, diethylene glycol benzyl ether, triethylene glycol methyl ether, triethylene glycol ethyl ether, triethylene glycol propyl ether, triethylene glycol butyl ether, triethylene glycol pentyl ether, triethylene glycol hexyl ether, triethylene glycol benzyl ether, tetraethylene glycol methyl ether, tetraethylene glycol ethyl ether, tetraethylene glycol propyl ether, tetraethylene glycol butyl ether, tetraethylene glycol pentyl ether, tetraethylene glycol hexyl ether, tetraethylene glycol benzyl ether, propylene glycol methyl ether, propylene glycol ethyl ether, propylene glycol propyl ether, propylene glycol butyl ether, propylene glycol hexyl ether, propylene glycol benzyl ether, dipropylene glycol methyl ether, dipropylene glycol propyl ether, dipropylene glycol butyl ether, dipropylene glycol pentyl ether, dipropylene glycol hexyl ether, and dipropylene glycol benzyl ether.

12. The compound of claim 1, wherein the compound is selected from the group of:
2-(2-(2-hexyloxyethoxy)ethoxy)ethyl 2-methyl-2-octyldecanoate, 2-(2-(2-hexyloxyethoxy)ethoxy)ethyl 2-methyl-2-hexyloctanoate, 2-(2-(3-hexyloxypropoxy)ethoxy)ethyl 2-ethyl-2-octyldecanoate, 2-(3-(2-hexyloxyethoxy)propoxy)ethyl 2-ethyl-2-octyldecanoate, 2-(3-(3-hexyloxypropoxy)propoxy)ethyl 2-ethyl-2-octyldecanoate, 2-(2-(2-butyloxyethoxy)ethoxy)ethyl 2-methyl-2-octyldecanoate, 2-(2-(2-butyloxyethoxy)ethoxy)ethyl 2-methyl-2-hexyloctanoate, 2-(2-(3-butyloxypropoxy)ethoxy)ethyl 2-ethyl-2-octyldecanoate, 2-(3-(2-butyloxyethoxy)propoxy)ethyl 2-ethyl-2-octyldecanoate, 2-(3-(3-butyloxypropoxy)propoxy)ethyl 2-ethyl-2-octyldecanoate, 2-(2-(2-ethoxyethoxy)ethoxy)ethyl 2-methyl-2-octyldecanoate, 2-(2-(2-ethoxyethoxy)ethoxy)ethyl 2-methyl-2-hexyloctanoate, 2-(2-(3-ethoxypropoxy)ethoxy)ethyl 2-ethyl-2-octyldecanoate, 2-(3-(2-ethoxyethoxy)propoxy)ethyl 2-ethyl-2-octyldecanoate, and 2-(3-(3-ethoxypropoxy)propoxy)ethyl 2-ethyl-2-octyldecanoate.

13. A lubricating oil composition comprising a compound of claim 1.

14. The lubricating oil composition of claim 13, wherein the lubricating oil composition is formulated as a coolant for an electric vehicle.

15. The lubricating oil composition of claim 13 having a kinematic viscosity at 100° C. as determined pursuant to ASTM D445 in the range from 1 to 140 cSt.

16. The lubricating oil composition of claim 13, which is a lubricating oil formulation comprising a compound of structural Formula F-I:

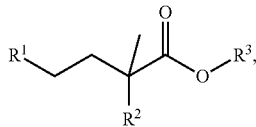

wherein $R^1$ and $R^2$ are independently each a hydrocarbyl group comprising at least two carbon atoms; and $R^3$ is a glycol ether or a polyglycol ether, as a first base stock.

17. The lubricating oil composition of claim 13, wherein the concentration of the first base stock, based on the total weight of the lubricating oil formulation, is in the range from 5 to 95 wt %.

18. A method for making an ester product comprising an ester compound of the structural Formula F-I:

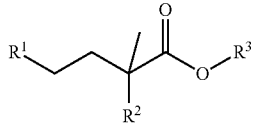

wherein $R^1$ and $R^2$ are each independently a hydrocarbyl group comprising at least two carbon atoms, and $R^3$ is a glycol ether or polyglycol ether;
the method comprising the steps of:
reacting a neo-acid of the structural Formula F-II as follows:

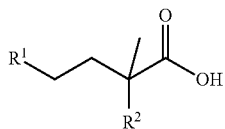

and/or an anhydride thereof with an alcohol of the Formula F-III as follows:

$R^3$—OH in the presence of an acid catalyst to obtain a reaction mixture, wherein $R^1$, $R^2$, and $R^3$ correspond to the $R^1$, $R^2$, and $R^3$ of Formula F-I, respectively; and
obtaining the ester product from the reaction mixture.

19. The method of claim 18, wherein $R^1$ and $R^2$ are each independently a C1 to C30 linear alkyl group.

20. The method of claim 19, wherein $R^1$ and $R^2$ are each independently selected from n-butyl, n-hexyl, n-octyl, n-decyl, and n-dodecyl.

21. The method of claim 18, wherein $R^3$ is a glycol ether is defined by the structural formula:

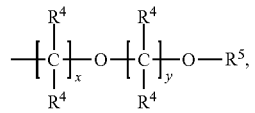

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from 0 to 10, and y is a value from 1 to 10.

22. The method of claim 18, wherein $R^3$ is a polyglycol ether of the structural formula:

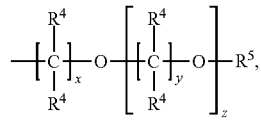

wherein each $R^4$ is the same or different and is hydrogen or a substituted or unsubstituted alkyl group (C1-C30), alkenyl group (C1-C30), alkoxy group (C1-C30), aryl group (C4-C30), or arylalkyl group (C5-C30), $R^5$ is hydrogen or a substituted or unsubstituted alkyl group (C1-C30), alkenyl group (C1-C30), alkoxy group (C1-C30), aryl group (C4-C30), or arylalkyl group (C5-C30), x is a value from 0 to 10, y is a value from 1 to 10, and z is a value from 0 to 100.

23. The method of claim 18, wherein the alcohol is selected from the group of methoxyethanol, ethoxyethanol, propoxyethanol, butoxyethanol, pentoxyethanol, hexyloxyethanol, phenoxyethanol, diethylene glycol methyl ether, diethylene glycol ethyl ether, diethylene glycol propyl ether, diethylene glycol butyl ether, diethylene glycol pentyl ether, diethylene glycol hexyl ether, diethylene glycol benzyl ether, triethylene glycol methyl ether, triethylene glycol ethyl ether, triethylene glycol propyl ether, triethylene glycol butyl ether, triethylene glycol pentyl ether, triethylene glycol hexyl ether, triethylene glycol benzyl ether, tetraethylene glycol methyl ether, tetraethylene glycol ethyl ether, tetraethylene glycol propyl ether, tetraethylene glycol butyl ether, tetraethylene glycol pentyl ether, tetraethylene glycol hexyl ether, tetraethylene glycol benzyl ether, propylene glycol methyl ether, propylene glycol ethyl ether, propylene glycol propyl ether, propylene glycol butyl ether, propylene glycol hexyl ether, propylene glycol benzyl ether, dipropylene glycol methyl ether, dipropylene glycol propyl ether, dipropylene glycol butyl ether, dipropylene glycol pentyl ether, dipropylene glycol hexyl ether, and dipropylene glycol benzyl ether.

24. The method of claim 18, wherein the neo-acid is one or more selected from the group of 2-ethyl-2-methylhexanoic acid; 2-methyl-2-propylheptanoic acid; 2-butyl-2-methyloctanoic acid; 2-methyl-2-pentylnonanoic acid; 2-hexyl-2-methyldecanoic acid; 2-heptyl-2-methylundecanoic acid; 2-methyl-2-octyldodecanoic acid; 2-decyl-2-methyltetradecanoic acid; 2-dodecyl-2-methylhexadecanoic acid; 2-methyl-2-tetradecyloctadecanoic acid; and 2-methyl-2-hexadecylicosanoic acid.

\* \* \* \* \*